United States Patent
Müller et al.

(10) Patent No.: US 6,444,828 B1
(45) Date of Patent: Sep. 3, 2002

(54) METHOD FOR PREPARING 1-ALKYL-PYRAZOL-5-CARBOXYLIC ACID ESTERS III

(75) Inventors: Nikolaus Müller, Monheim; Michael Matzke, Wuppertal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/762,626

(22) PCT Filed: Aug. 4, 1999

(86) PCT No.: PCT/EP99/05641

§ 371 (c)(1),
(2), (4) Date: Feb. 9, 2001

(87) PCT Pub. No.: WO00/10978

PCT Pub. Date: Mar. 2, 2000

(30) Foreign Application Priority Data

Aug. 17, 1998 (DE) ......................... 198 37 067

(51) Int. Cl.[7] .............................................. C07D 231/10
(52) U.S. Cl. .................................................... 548/374.1
(58) Field of Search ........................................ 548/374.1

(56) References Cited

U.S. PATENT DOCUMENTS

| | | | |
|---|---|---|---|
| 3,557,095 A | 1/1971 | DeWald | 260/239.3 |
| 5,250,534 A | 10/1993 | Bell et al. | 514/258 |
| 5,346,901 A | 9/1994 | Bell et al. | 514/258 |
| 5,426,107 A | 6/1995 | Bell et al. | 514/234.2 |
| 5,719,283 A | 2/1998 | Bell et al. | 544/262 |
| 5,977,378 A * | 11/1999 | Muller et al. | 548/374.1 |

FOREIGN PATENT DOCUMENTS

| | | |
|---|---|---|
| EP | 0029363 | 5/1981 |
| EP | 9854142 | 7/1998 |
| JP | 2292263 | 12/1990 |
| WO | 94/28902 | 12/1994 |

OTHER PUBLICATIONS

Organikum, 19th ed., p. 490, (date unavailable), H.G.O. Becker et al Allgemeine Arbeitsvorschrift für die Esterkondensation und die Glycidestersynthese nach Darzens (Tab. 7.163), 1962.

Austr. J. Chem. 36, (month unavailable) 1983, pp. 135–147, Huppatz, "Systemic Fungicides. The Synthesis of Certain Pyrazole Analogues of Carboxin".

Chem. Ber, 59, (month unavailable), 1926, pp. 1282–1302, Auwers et al, "Über die Isomerie–Verhältinsse in der Pyrazol–Reihe, IX: Über 1.3–und 1.5–Dialkyl–pyrazole und verwandte Verbindungen".

* cited by examiner

Primary Examiner—T. A. Solola
Assistant Examiner—Joseph Murray
(74) Attorney, Agent, or Firm—Joseph C. Gil; Richard E. L. Henderson; Diderico van Eyl

(57) ABSTRACT

1-Alkyl-pyrazole-5-carboxylic esters are obtained with surprisingly low proportions of 1-alkyl-pyrazole-3-carboxylic esters if a 2,4-diketo ester and/or an enolate thereof is reacted with an alkylhydrazine and/or a corresponding alkylhydrazinium salt, if appropriate, in the presence of a solvent and/or of water, in such a manner that during at least about 90% of the reaction free alkylhydrazine is present.

10 Claims, No Drawings

METHOD FOR PREPARING 1-ALKYL-PYRAZOL-5-CARBOXYLIC ACID ESTERS III

BACKGROUND

The present invention relates to a particularly advantageous process for preparing 1-alkyl-, in particular 1,3-dialkyl-pyrazole-5-carboxylic esters, from 2,4-diketocarboxylic esters and alkylhydrazines, where some or all of the 2,4-diketocarboxylic ester may be employed in the form of its enolate and some of the alkylhydrazine may be employed in the form of an alkylhydrazinium salt.

It is known to prepare 1-alkyl-pyrazole-5-carboxylic esters by reacting 2,4-diketocarboxylic esters and alkylhydrazines with each other. This gives isomer mixtures which generally contain predominantly the isomer which is undesired here, which then necessitates a complicated separation process and keeps the yield of the desired isomer low. Thus, reaction of ethyl 2, 4-dioxo-pentanecarboxylate, which is initially charged, with methylhydrazine gives a 1:1 mixture of 1,5-dimethyl-pyrazole-3-carboxylate and the corresponding 2,5-dimethyl isomer (Austr. J. Chem. 36, 135–147 (1983)). Other authors report even more unfavorable ratios of 35:65 (Chem. Ber. 59, 1282 (1926)), which were confirmed in comparative laboratory experiments, for this reaction. The same authors obtained even worse results (isomer ratio 15:85) with analogous etherified enols, for example with O-ethyl acetone oxalate and methylhydrazine.

EP-A 029 363 also describes the synthesis of N-alkyl-substituted pyrazolecarboxylic esters having long alkyl radicals from diketo ester enolate which is initially charged and alkylhydrazine. However, the pyrazole which is isolated in moderate yields is again not the desired pyrazole, since the N-alkyl substituent and the carboxyl group are in 1,3-position and not, as desired, in 1,5-position. In these reactions, either the free alkylhydrazines are reacted with diketo ester which is initially charged, or the sodium enolate of the diketo ester and an alkylhydrazinium salt are initially charged and the hydrazine is liberated with basic compounds (such as sodium hydroxide or sodium carbonate) from the hydrazinium salt.

According to EP-A 854 142, 1-alkyl-pyrazole-5-carboxylic esters are prepared by reacting the enolate of a 2,4-diketocarboxylic ester in the presence of a solvent, for example an alcohol, with an alkylhydrazinium salt. The alkylhydrazinium salt has to be prepared from alkylhydrazine using an acid in the presence of an alcohol. Here, the isomer ratios are favorable, but the amount of undesired isomer is not insignificant and the yield is therefore still not optimal.

There is therefore still a need for a process for the selective preparation of 1-alkyl-pyrazole-5-carboxylic esters in which considerably less of the corresponding 1,3-isomer is formed than in the known processes.

DESCRIPTION

This invention, accordingly, provides a process for preparing 1-alkyl-pyrazole-5-carboxylic esters of the formula (I)

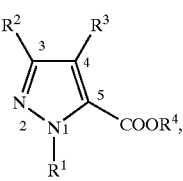

(I)

in which
$R^1$ and $R^4$ independently of one another each represent straight-chain or branched, optionally halogen-substituted $C_1$–$C_6$-alkyl, $C_3$–$C_7$-cycloalkyl or optionally substituted $C_7$–$C_{12}$-aralkyl and
$R^2$ and $R^3$ independently of one another each represent hydrogen, straight-chain or branched, optionally halogen-substituted $C_1$–$C_6$-alkyl, optionally halogen-substituted $C_3$–$C_7$-cycloalkyl or optionally substituted $C_7$–$C_{12}$-aralkyl,
characterized in that a 2,4-diketo ester of the formula

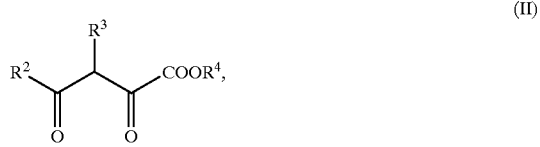

(II)

in which
$R^2$, $R^3$ and $R^4$ are each as defined in formula (I),
and/or an enolate thereof is reacted
with an alkylhydrazine of the formula

(III), in which
$R^1$ is as defined in formula (I),
and/or a corresponding alkylhydrazinium salt,
if appropriate in the presence of a solvent and/or of water,
in such a manner that during at least 90% of the reaction free alkylhydrazine of the formula (III) is present.

$C_7$–$C_{12}$-aralkyl, preferably benzyl, and $C_6$–$C_{10}$-aryl (mentioned hereinbelow), preferably phenyl (mentioned hereinbelow), may in each case contain, for example, up to two substituents from the group of the halogen atoms and the $C_1$–$C_4$-alkyl radicals.

Preferred diketo esters of the formula (II) are those where the radicals $R^2$ and $R^3$ independently of one another each represent hydrogen, straight-chain or branched $C_1$–$C_4$-alkyl, $C_3$–$C_6$-cycloalkyl or optionally substituted benzyl, or also those where the radical $R^4$ represents straight-chain or branched $C_1$–$C_4$-alkyl.

Particular preference is given to 2,4-diketo esters of the formula (II) where $R^2$ and $R^4$ each represent $C_1$–$C_4$-alkyl and $R^3$ represents H.

Among the alkylhydrazines of the formula (III), preference is given to those where $R^1$ represents straight-chain or branched $C_1$–$C_4$-alkyl or optionally substituted benzyl.

Diketo esters of the formula (II) can be prepared by a conventional method by condensation of a dialkyl ketone of the formula

(IV)

in which
$R^2$ and $R^3$ are each as defined for formula (I),
with an oxalic ester of the formula

(V), in which
$R^4$ is as defined for formula (I).

The reaction is carried out in the presence of basic condensing agents, for example alkoxides, and of a solvent. The diketo ester of the formula (II), which is obtained as the enolate, can be liberated from the resulting crude reaction mixture by acidification and can be obtained in pure form by customary methods, for example by extraction with an organic solvent, concentration and distillation (see Organicum, 16th edition, 1976, p.472).

Suitable solvents for the reaction of the dialkyl ketones of the formula (IV) with oxalic esters of the formula (V) are, for example, alcohols such as methanol, ethanol, n-propanol, i-propanol and n-, i-, s- and t-butanol. The alkoxide can be prepared by dissolving an alkali metal or alkaline earth metal in the alcohol which corresponds to the alkoxide.

The diketo ester of the formula (II) is reacted according to the invention with the alkylhydrazine of the formula (III) in such a manner that during at least 90% of the reaction free alkylhydrazine of the formula (III) is present. Preferably, free alkylhydrazine is present during 95 to 100% of the reaction. "x% of the reaction" is understood here as meaning that x% of the total diketo ester of the formula (II) which has been employed has been converted.

The most simple manner by which this can be achieved is by initially charging the alkylhydrazine of the formula (III) in an equimolar amount or in excess, if appropriate in a solvent or water, and slowly adding the diketo ester of the formula (II), if appropriate in a solvent. By initially charging the alkylhydrazine of the formula (III), it is ensured that even when stoichiometric amounts of alkylhydrazine and diketo esters are employed, free alkylhydrazine of the formula (III) is present during almost 100% of the reaction.

It is also possible to initially charge a small amount of free alkylhydrazine, for example 10 to 20% by weight of the total amount, and to add simultaneously the remainder of the alkylhydrazine and the diketo ester, both if appropriate in a solvent or water. It is advantageous here to add a small amount of alkylhydrazine first.

Preference is given to using the diketo ester of the formula (II) in the form of an enolate of the formula (VI):

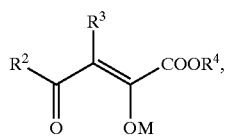

(VI)

in which
 $R^2$, $R^3$ and $R^4$ are each as defined for formula (I) and
 M represents an equivalent of an alkali metal or alkaline earth metal.

If alkylhydrazinium salts are employed, these may correspond to the formula (VII)

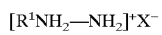 (VII), in which
 $R^1$ is as defined for formula (I) and
 $X^-$ represents the anion of an organic or inorganic acid.

Suitable anions $X^-$ of inorganic acids are, for example, chloride, bromide, fluoride, hydrogen sulfate, dihydrogen phosphate and hydrogen carbonate. Preferred anions $X^-$ are those of organic acids. In this case, $X^-$ in particular represents $R^5COO^-$, where $R^5$ represents a $C_1$–$C_{10}$-aliphatic or a $C_6$–$C_{12}$-aromatic radical, each of which may optionally be substituted. $R^5$ preferably represents formate, acetate, propionate, butyrate or benzoate.

$R^5$ together with the $COO^-$-moiety may also represent an anion of a polybasic organic acid. Examples are anions of oxalic, malonic, succinic, glutaric, adipic, maleic, fumaric, malic, tartaric and citric acid, and they may in each case be mono- or polyanions. Such anions may contain one or more $COO^-$-moieties and if appropriate, additionally also COOH radicals.

In the case of anions of polybasic organic acids, the alkylhydrazine can be employed in equivalent amounts, based on the acid, i.e. in amounts which are equal to the number of acid groups.

In order that the free alkylhydrazine of the formula (III) required according to the invention is present even when alkylhydrazinium salts are employed, it is advantageous to add free alkylhydrazine of the formula (III) to the alkylhydrazinium salt prior to the reaction with the diketo ester or its enolate.

The process according to the invention can be carried out, for example, by metering in a diketo ester enolate of the formula (VI), for example in the form of a crude reaction mixture from the condensation reaction of a ketone of the formula (I) and an oxalic ester of the formula (V), to a mixture of an as equimolar amount as possible of an alkylhydrazinium salt of the formula (VII) which contains a proportion of free alkylhydrazine of the formula (III). By reaction with the alkylhydrazinium salt of the formula (VII), the diketo ester enolate of the formula (VI) forms in situ the free diketo ester of the formula (II) and free alkylhydrazine of the formula (III), which spontaneously react to give the desired pyrazole of the formula (I).

However, it is also possible to add an alkylhydrazinium salt of the formula (VII) in a mixture with a free alkylhydrazine of the formula (III), if appropriate in the presence of a solvent or water, to a diketo ester of the formula (II) which has been initially charged, or to an enolate thereof of the formula (VI). Thus, it is ensured that diketo ester which is liberated from the enolate always encounters free alkylhydrazine.

If solvents and/or water are used, the total amounts of solvent and water employed are generally chosen so that stirrable suspensions or solutions are present. The total amount of solvent plus water per mole of reaction mixture may, for example, be n corresponds to the valency of M.

The dialkyl ketone and the alkoxide are preferably employed in approximately equimolar amounts. Altogether, it is possible to employ, for example, from 0.9 to 1.1 mol of oxalic ester of the formula (V) and from 0.9 to 1.1 mol of alkoxide, for example of the formula (VIII), per 0.9 to 0.99 mol of dialkyl ketone of the formula (IV).

If the alkylhydrazinium salt of the formula (VII) is prepared from an alkylhydrazine of the formula (III) and a carboxylic acid, for example of the formula $R^5COOH$, it is advantageous to choose the molar ratio of the two starting materials such that, after formation of the alkylhydrazinium salt, for example from 1 to 200 mol % of free alkylhydrazine of the formula (III) are present.

An excess of carboxylic acid, for example of the formula $R^5COOH$, is only then advantageous if the alkoxide, for example from the preparation of a diketo ester enolate of the formula (VI), is present in excess. The excess alkoxide can then be neutralized with the excess acid.

The reaction temperatures for the reaction according to the invention may be, for example, between −20 and +100° C. Preference is given to from 0 to 80° C., particularly preferably from 0 to 50° C. These temperatures may also be maintained during any subsequent stirring.

The reaction time (=time for mixing the reaction partners+subsequent stirring time) may, for example, be between 0.5 and 12 hours. It is preferably between 1 and 8 hours, particularly preferably between 2 and 5 hours.

The following 2,4-diketo ester components are preferably employed for the process according to the invention: ethyl 2,4-diketopentanecarboxylate as sodium, lithium, between 100 and 2000 ml. This amount is preferably from 200 to 1000 ml, particularly preferably from 250 to 500 ml. The total amount of solvent plus water may comprise, for example, from 10 to 60% by weight, preferably from 15 to 40% by weight, of water.

It is advantageous to use such an amount of free alkylhydrazine of the formula (III) and, if appropriate, such an amount of alkylhydrazinium salt of the formula (VII) for the process according to the invention that, after the reaction has ended, for example from 0.1 to 200 mol % of free alkylhydrazine of the formula (III) are still present (based on the diketo ester employed or its enolate). This amount is particularly preferably from 1 to 50 mol %, in particular from 5 to 20 mol %.

If the preparation of the diketo ester enolate of the formula (VI) is carried out in the presence of alkoxide, the amount of alkoxide may vary within wide limits. Preference is given to using at least 90 mol % of alkoxide, based on the ketone of the formula (IV).

If the diketo ester of the formula (II) is prepared in a prior step as described above from a dialkyl ketone of the formula (IV) and an oxalic ester of the formula (V), their molar ratios may also vary. Preference is given to carrying out the reaction with a slight excess of oxalic ester, for example with a substoichiometric quantity of in each case from 1 to 10 mol % of dialkyl ketone of the formula (IV) and alkoxide of the formula

   (VIII), in which

M is as defined for formula (VI), $R^6$ represents C1–C$_4$-alkyl and potassium or magnesium enolate salts, ethyl 2,4-diketohexanecarboxylate, ethyl 2,4-diketoheptanecarboxylate, ethyl 2,4-diketooctanecarboxylate and ethyl 2,4-diketo-3-ethylpentanecarboxylate (in each case in the form of their sodium, lithium, potassium or magnesium enolate salts) or methyl, n-propyl, i-propyl and n-, i-, s- and t-butyl esters of the abovementioned diketocarboxylic acids in the form of the above-mentioned enolate salts.

Preferred alkylhydrazines of the formula (III) are methyl-, ethyl-, n-propyl-, i-propyl-, n-butyl-, t-butyl-, benzyl- and n-pentylhydrazine.

A general embodiment of the process according to the invention is illustrated below using the reaction of ethyl 2,4-diketoheptanecarboxylate with methylhydrazine as an example:

Initially, the sodium salt of ethyl 2,4-diketoheptanecarboxylate is prepared from 2-pentanone and diethyl oxalate using sodium ethoxide in ethanol as auxiliary base, in a similar way to known procedures (see, for example, Organicum, 19th ed., p. 490 (1993)). This solution is kept at 50° C. to prevent precipitation of the enolate and, over a period of 1 hour, added to a mixture of methylhydrazine and acetic acid (molar ratio 1.1:1) which has been prepared beforehand. Stirring is continued, the excess ethanol is distilled off and the mixture is mixed with toluene and, if appropriate, with more water. To improve phase separation, it is possible, if appropriate, to add a suitable surfactant, for example an alkanesulfonate, and/or to increase the ion concentration in the aqueous phase, for example by addition of a salt, such as an alkali metal halide. The toluene phase is then separated off and the aqueous phase is extracted two more times with toluene. The organic phases are combined and then re-extracted with water. The water may, if appropriate, contain an acid and/or a salt. The toluene solution of the crude pyrazole is subsequently concentrated by distilling off the solvent, and the residue is subjected to fractional distillation under reduced pressure. The two isomeric pyrazoles can be isolated in pure form without any major separation costs.

The process according to the invention yields the desired 1-alkyl-pyrazole-5-carboxylic esters generally in amounts of more than 8 times, frequently in 10 times the amount or even higher amounts, in each case based on the undesired wrong isomer (=1-alkyl-pyrazole-3-carboxylic ester).

It is extremely surprising that the process according to the invention has such an extraordinarily favorable effect on the regioselectivity of the formation of the desired 1-alkyl-pyrazole-5-carboxylic esters. If, during the reaction, no free alkylhydrazine of the formula (III) is present, as is the case in the prior art (see also Comparative Example), the undesired isomers are obtained in a higher amount than the desired isomers of the formula (I), or the desired isomer is obtained in a considerably lower excess. It has to be mentioned as being particularly surprising that even a small excess of free alkylhydrazine effects the substantial inversion of the isomer distribution shown.

1-Alkyl-pyrazole-5-carboxylic esters of the formula (I) are usefull intermediates for preparing pharmaceutically active compounds having vasoactive and/or spasmolytic action (see EP published specification 463 756, EP published specification 526 004, WO 94/28902 and DE published specification 19 27 429), and also for preparing pesticides having insecticidal and acaricidal action (see JP published specification 89-114 466).

The invention is further described in the following illustrative examples in which all parts and percentages are by weight unless otherwise indicated.

EXAMPLES

Example 1

10.4 g of methylhydrazine were initially charged in 50 ml of ethanol and, with stirring and external cooling, admixed with a solution of 42.9 g of ethyl 2,4-diketoheptanecarboxylate in 50 ml of ethanol, during which the internal temperature was kept at 5 to 10° C. (time for the dropwise addition: 10 minutes). The solution was stirred at 5 to 10° C. for another 30 minutes, the solvent and the water which had been formed were distilled off and the residue was fractionated under reduced pressure. The desired ethyl 1-methyl-3-n-propyl-pyrazole-5-carboxylate passed over at 125 to 128° C. (13 mm). The yield was 78.3% of theory. By further distillation (166 to 168° C./13 mm), the undesired isomer (=ethyl 1-methyl-5-n-propyl-pyrazole-3-carboxylate) was obtained in a yield of 7.9% of theory. Thus, the isomer ratio was approximately 10:1 in favor of the desired isomer.

Example 2
(Comparison)

Reversing the procedure of Example 1, 42.9 g of ethyl 2,4-diketoheptanecarboxylate were initially charged in 50 ml of ethanol, and 10.4 g of methylhydrazine were added dropwise at 5 to 10° C. with stirring and external cooling over a period of 1 hour. After work-up and purification by distillation according to the procedure of Example 1, 40.5% of theory of ethyl 1-methyl-3-n-propyl-pyrazole-5-carboxylate and 51% of theory of ethyl 1-methyl-5-n-propyl-pyrazole-3-carboxylate were obtained. Thus, the isomer ratio was approximately 5:4 in favor of the undesired isomer.

Example 3

1462 g of diethyl oxalate were initially charged in a 1l four-necked flask, and 776 g of pentan-2-one were added. With stirring at 25 to 40° C., 3400 g of a 20% strength by weight solution of sodium ethoxide in ethanol were metered in over a period of 1 hour. The reaction mixture was stirred at 50° C. for 1 hour and then under reflux for 1 hour, and subsequently cooled to 50° C. again. During the subsequent stirring, 506 g (10.95 mol) of methylhydrazine were initially charged in another flask, and 600 g (10 mol) of acetic acid were added dropwise at 5 to 30° C. over a period of 1 hour, and the mixture was subsequently cooled to 10° C. The ethyl 2,4-diketoheptanecarboxylate enolate solution which had been prepared first and which had been kept at 50° C. was added dropwise to this mixture over a period of 2 hours, during which the temperature of the reaction mixture was kept between 8 and 15° C. and the temperature of the ester enolate solution was kept at 45 to 55° C. After the addition had ended, a further 60 g of glacial acetic acid were added and the solvent was distilled off, until a bottom temperature of 88° C. was reached. The residue was cooled and admixed with stirring with 2000 ml of toluene, 5000 ml of water, 500 g of a surfactant (Mersolat® H30) and 20 g of sodium chloride. The aqueous phase was separated off and extracted with 200 ml of toluene. The organic phases were combined and washed with 2000 g of 5% strength by weight of aqueous sulfuric acid and 2000 ml of water. The organic phases were subsequently concentrated at 60 mbar until a bottom temperature of 70° C. was reached. This gave 1748 g of a brown oil containing 74.7% by weight of ethyl 1-methyl-3-n-propyl-pyrazole-5-carboxylate and 5.8% by weight of the undesired ethyl 1-methyl-5-n-propyl-pyrazole-3-carboxylate, corresponding to a crude yield of 73.9% of theory of the desired compound. Thus, the isomer ratio was approximately 13:1 in favor of the desired isomer.

Distillation under reduced pressure gave as first fraction 1152 g of the desired product having a boiling point of 121° C. at 11 mbar and a purity (GC) of 99.9%. The yield of pure product was 65% of theory.

Although the present invention has been described in detail with reference to certain preferred versions thereof, other variations are possible. Therefore, the spirit and scope of the appended claims should not be limited to the description of the versions contained therein.

What is claimed:

1. A process for preparing 1-alkyl-pyrazole-5-carboxylic esters of the formula

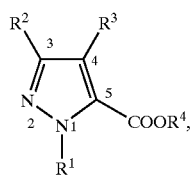

(I)

in which

R$^1$ and R$^4$ independently of one another each represent straight-chain or branched, optionally halogen-substituted C$_1$–C$_6$-alkyl, optionally halogen-substituted C$_3$–C$_7$-cycloalkyl or optionally substituted C$_7$–C$_{12}$-aralkyl and R$^2$ and R$^3$ independently of one another each represent hydrogen, straight-chain or branched, optionally halogen-substituted C$_1$–C$_6$-alkyl, C$_3$–C$_7$-cycloalkyl or optionally substituted C$_7$–C$_{12}$-aralkyl, wherein a 2,4-diketo ester of the formula

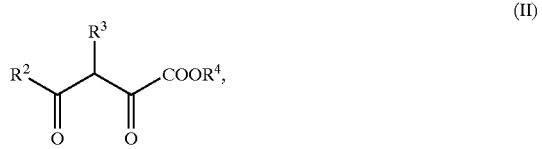

(II)

in which

R$^2$, R$^3$ and R$^4$ are each as defined in formula (I), and/or an enolate thereof is reacted with an alkylhydrazine of the formula

R$^1$—NH—NH$_2$ (III), in which

R$^1$ is as defined in formula (I), and/or a corresponding alkylhydrazinium salt, if appropriate in the presence of a solvent and/or of water, in such a manner that during at least 90% of the reaction free alkylhydrazine of the formula (III) is present.

2. The process as claimed in claim 1, wherein in the formulae

R$^1$ represents straight-chain or branched C$_1$–C$_4$-alkyl or optionally substituted benzyl, R$^2$ and R$^3$ independently of one another each represent hydrogen, straight-chain or branched, optionally halogen-substituted C$_1$–C$_4$-alkyl, optionally halogen-substituted C$_3$–C$_6$-cycloalkyl or optionally substituted benzyl and R$^4$ represents straight-chain or branched C$_1$–C$_4$-alkyl.

3. The process as claimed in claim 1, wherein during from about 95 to about 100% of the reaction free alkylhydrazine of the formula (III) is present.

4. The process as claimed in claim 1, wherein the alkylhydrazine of the formula (III) is initially charged in an equimolar amount or in excess and the diketo ester of the formula (II) is slowly added.

5. The process as claimed in claim 1, wherein a small amount of free alkylhydrazine is initially charged and the remainder of the alkylhydrazine and the diketo ester are added simultaneously.

6. The process as claimed in claim 1, wherein the diketo ester of formula (II) is employed in the form of its enolate of the formula (VI)

in which

R$^2$, R$^3$ and R$^4$ are each as defined in claim 1 for formula (I) and

M represents an equivalent of an alkali metal or alkaline earth metal.

7. The process as claimed in claim 1, wherein the alkylhydrazinium salts employed are those of the formula (VII)

$$[R^1NH_2\text{—}NH_2]^+X^- \qquad\qquad (VII),$$

in which

R$^1$ is as defined in claim 1 for formula (I) and

X$^-$ represents the anion of an organic or inorganic acid.

8. The process as claimed in claim 1, the 2,4-diketo ester is employed in the form of its enolate as obtained as a crude reaction mixture in the condensation of a dialkyl ketone of the formula $$R^2\text{—}\underset{\underset{O}{\|}}{C}\text{—}CH_2\text{—}R^3, \qquad\qquad (IV)$$

in which

R$^2$ and R$^3$ are each as defined in claim 1 for formula (I) with an oxalic ester of the formula $$R^4OOC\text{—}COOR^4 \qquad\qquad (V),$$

in which

R$^4$ is as defined in claim 1 for formula (I), and the enolate is metered into a mixture of an alkylhydrazinium salt of the formula $$[R^1NH_2\text{—}NH_2]^+X^- \qquad\qquad (VII),$$

which

R$^1$ is as defined in claim 1 for formula (I) and

X$^-$ represents the anion of an organic or inorganic acid, and which contains a proportion of free alkylhydrazine of the formula (III).

9. The process as claimed in claim 1, wherein a sufficient amount of free alkylhydrazine of the formula (III) and a sufficient amount of alkylhydrazinium salt are used that, after the reaction has ended, from about 0.1 to about 200 mol % of free alkylhydrazine of the formula (III) are still present, based on the diketo ester employed or its enolate.

10. The process as claimed in claim 1, wherein the process is carried out at temperatures from about −20 to about +100° C. and with reaction times from about 0.5 to about 12 hours.

* * * * *